US 7,792,578 B2

(12) United States Patent
Belk et al.

(10) Patent No.: US 7,792,578 B2
(45) Date of Patent: Sep. 7, 2010

(54) METHOD AND DEVICE FOR DELIVERING ANTI-TACHYCARDIA PACING THERAPY

(75) Inventors: Paul A. Belk, Maple Grove, MN (US); Troy E. Jackson, New Brighton, MN (US)

(73) Assignee: Medtronic, Inc., Minneapolis, MN (US)

( * ) Notice: Subject to any disclaimer, the term of this patent is extended or adjusted under 35 U.S.C. 154(b) by 370 days.

(21) Appl. No.: 11/675,270

(22) Filed: Feb. 15, 2007

(65) Prior Publication Data
US 2007/0191896 A1    Aug. 16, 2007

Related U.S. Application Data

(60) Provisional application No. 60/773,483, filed on Feb. 15, 2006.

(51) Int. Cl.
*A61N 1/00* (2006.01)
(52) U.S. Cl. .......................................................... 607/5
(58) Field of Classification Search .................. 607/4, 607/12, 14, 51
See application file for complete search history.

(56) References Cited

U.S. PATENT DOCUMENTS

| | | | |
|---|---|---|---|
| 4,830,006 A | | 5/1989 | Haluska et al. |
| 4,872,459 A | * | 10/1989 | Pless et al. .................... 607/15 |
| 5,836,971 A | | 11/1998 | Starkweather |
| 6,088,614 A | * | 7/2000 | Swanson .................... 600/510 |
| 6,167,308 A | | 12/2000 | DeGroot |
| 2003/0083703 A1 | | 5/2003 | Zhu et al. |
| 2004/0106956 A1 | | 6/2004 | Sharma et al. |

FOREIGN PATENT DOCUMENTS

WO    2006105457 A1    10/2006

OTHER PUBLICATIONS

Soejima, Kyoko; "The N + 1 Difference: A New Measure for Entrainment Mapping", Journal of the American College of Cardiology; vol. 37, No. 5, Apr. 2001, pp. 1386-1394.
Callans, David J. et al.; "Characterization of Return Cycle Responses Predictive of Successful Pacing-Mediated Termination of Ventricular Tachycardia"; Journal of the American College of Cardiology; vol. 25, No. 1, 1995; pp. 47-53.
Arenal A. et al.; "First Postpacing Interval Variability During Right Ventricular Stimulation: A Single Algorithm for the Differential diagnosis of Regular Tachycardias"; Circulation (Journal of the American Heart Association); Aug. 18, 1998, vol. 98, NR. 7; pp. 671-677.
PCT International Search Report; PCT/US2007/062215.

* cited by examiner

*Primary Examiner*—George Manuel
*Assistant Examiner*—Shubatra Narayanaswamy
(74) *Attorney, Agent, or Firm*—Michael C. Soldner

(57) ABSTRACT

A method and device for delivering anti-tachycardia pacing (ATP) therapy that includes an electrode to sense cardiac signals and to deliver the therapy, sensing circuitry, electrically coupled to the electrode, to detect the tachycardia event in response to the sensed cardiac signals, and a processor to control delivery of the therapy. The processor determines adjustments to the delivered therapy, the adjustments being linearly dependent on characteristics of the tachycardia event.

12 Claims, 8 Drawing Sheets

METHOD AND DEVICE FOR DELIVERING ANTI-TACHYCARDIA PACING THERAPY

CROSS REFERENCE TO RELATED APPLICATION

The present application claims priority and other benefits from U.S. Provisional Patent Application Ser. No. 60/773,483, filed Feb. 15, 2006, entitled "DEVICE FOR DELIVERING ANTI-TACHYCARDIA PACING THERAPY", incorporated herein by reference in its entirety.

CROSS-REFERENCE TO RELATED APPLICATIONS

Cross-reference is hereby made to the commonly assigned related U.S. Applications, Ser. No. 11/675,284, entitled "METHOD AND DEVICE FOR DELIVERING ANTI-TACHYCARDIA PACING THERAPY", to Belk et al.; Ser. No. 11/675,297, entitled "METHOD AND DEVICE FOR DELIVERING ANTI-TACHYCARDIA PACING THERAPY", to Belk et al.; Ser. No. 11/675,303, entitled "METHOD AND DEVICE FOR DELIVERING ANTI-TACHYCARDIA PACING THERAPY", to Belk et al.; and Ser. No. 11/675,312, entitled "METHOD AND DEVICE FOR DELIVERING ANTI-TACHYCARDIA PACING THERAPY", to Belk et al.; all filed concurrently herewith and incorporated herein by reference in their entirety.

BACKGROUND OF THE INVENTION

The present invention relates generally to a method and apparatus for treating a tachycardia event in a medical device, and, more specifically, the present invention relates to adjusting delivery of anti-tachycardia pacing regimens in a medical device.

A typical pacemaker/cardioverter/defibrillator (PCD) device has the capability of providing a variety of anti-tachycardia pacing regimens. Normally, these regimens are applied according to a pre-programmed sequence, and each regimen includes a predetermined number of pacing pulses. After the series of pacing pulses is delivered, the device checks to determine whether the series of pulses was effective in terminating the detected tachycardia. Typically, termination is confirmed by a return to either a sinus rhythm or demand-paced rhythm, in which successive spontaneous depolarizations are separated by at least a defined interval. If the tachycardia is not terminated, the PCD device delivers a subsequent series of pacing pulses having modified pulse parameters, e.g. reduced inter-pulse intervals and/or an altered number of pulses. The typical PCD device bases future treatment on whether the tachycardia has been terminated by confirming a return to normal rhythm. Devices which function according to the basic methodology described above are disclosed in U.S. Pat. No. 4,830,006 issued to Haluska et al., U.S. Pat. No. 5,836,971 issued to Starkweather and U.S. Pat. No. 5,846,263 issued to Peterson et al.

Recent efforts have focused on modifying subsequent anti-tachycardia pacing regimens based on feedback received from previous anti-tachycardia pacing regimens. As described in U.S. Pat. No. 6,167,308 issued to DeGroot, if a PCD device determines that a particular pacing regimen, if continued, would likely not result in termination of the tachycardia, then either a new anti-tachycardia pacing regimen having modified pulse parameters is employed or the device delivers a high energy cardioversion pulse. To accomplish this result, the device first delivers a short series of pacing pulses at the defined parameters of the pacing pulse regimen, and then interrupts delivery of pacing pulses to await the next spontaneous depolarization and determine the return cycle length. The device then resumes delivery of the pacing pulse regimen for a second, greater number of pacing pulses, and again measures the return cycle length following the last pacing pulse. In the event that no increase in the return cycle occurs following the delivery of the longer series of pacing pulses, the device terminates the pacing pulse regimen presently underway, and initiates the next scheduled therapy, which may be a pacing pulse regimen, (preferably at a shorter inter-pulse interval) or a cardioversion shock. Pacing pulse regimens are a preferred first treatment method for tachycardias because cardioversion shocks are more uncomfortable for the patient and require a greater amount of energy.

BRIEF DESCRIPTION OF THE DRAWINGS

Aspects and features of the present invention will be appreciated as the same becomes better understood by reference to the following detailed description of the embodiments of the invention when considered in connection with the accompanying drawings, wherein:

FIGS. 4A-4E is a diagram of a heart with a reentrant tachycardia circuit and a pacing electrode for delivering ATP therapy;

DETAILED DESCRIPTION

Figure 1:
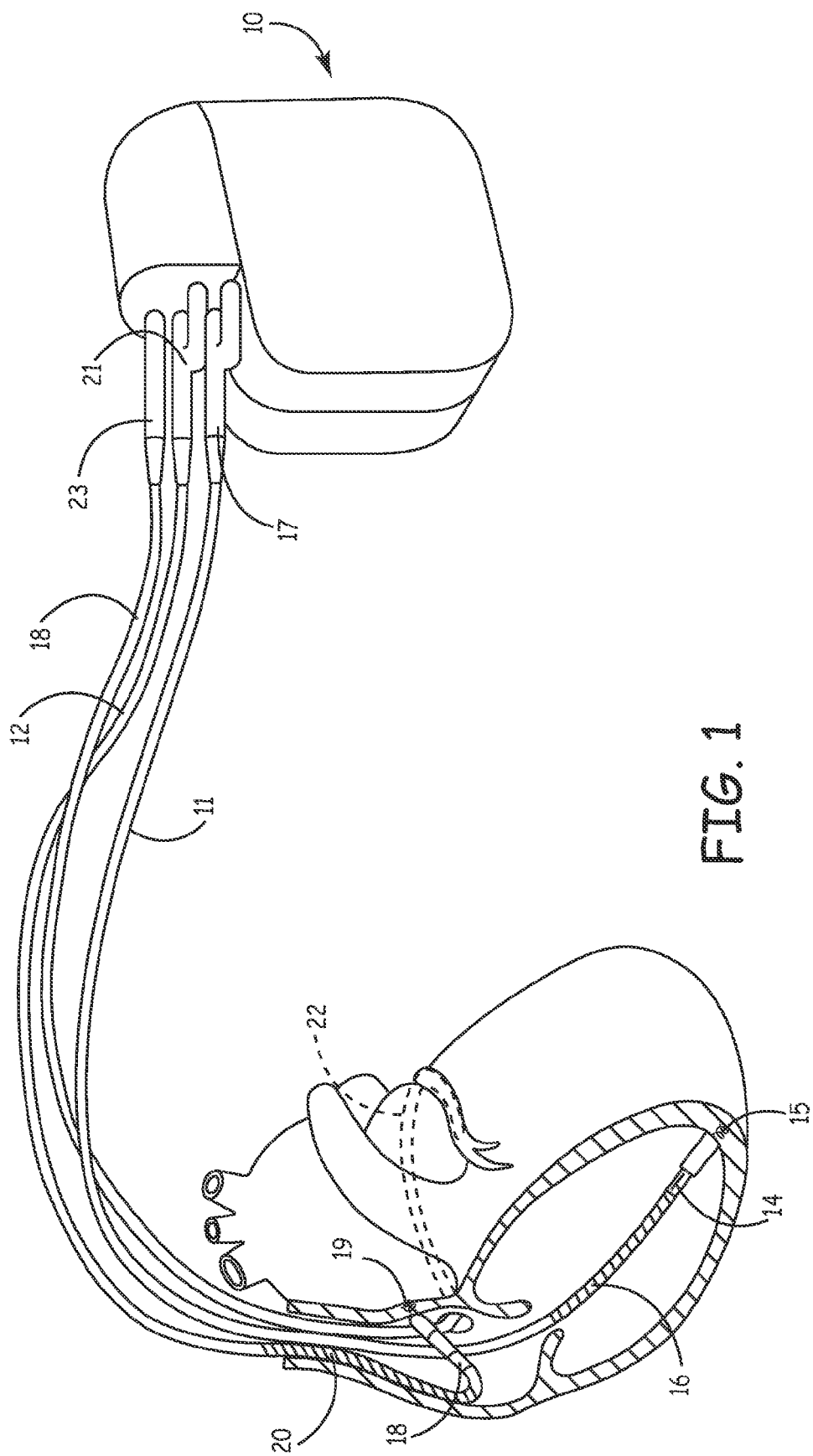
FIG. 1 is a schematic diagram of a pacemaker/cardioverter/defibrillator and lead set of a type in which the present invention may be usefully practiced.

FIG. 1 shows pacemaker/cardioverter/defibrillator PCD device 10, right ventricular lead 11, atrial/SVC lead 12, and coronary sinus lead 13. PCD device 10 delivers electrical pulses for anti-tachycardia pacing (ATP) therapy, cardioversion, and defibrillation through leads 11-13. In the present invention, device 10 provides customized ATP therapy for terminating reentrant tachycardia based upon analysis of the return cycle length (RCL) of a preceding train of ATP pulses. ATP therapy may be used to terminate a reentrant tachycardia located in either the atrial or ventricular regions of the heart.

Located adjacent the distal end of right ventricular lead 11 are ring electrode 14, tip electrode 15, and elongated coil electrode 16. At the proximal end of right ventricular lead 11 is a bifurcated connection 17, which connects electrodes 14, 15, and 16 to circuitry within device 10. Electrodes 14 and 15 are used to deliver ventricular anti-tachycardia pacing (ATP) pulses, and for sensing ventricular depolarizations or R-waves, while electrode 16 is used to deliver defibrillation or cardioversion shocks.

Atrial/SVC lead 12 also includes three electrodes 18-20. Located adjacent the J-shaped distal end of atrial lead 12 are a second ring electrode 18 and tip electrode 19. Located proximal to ring electrode 18 is elongated coil electrode 20. At the proximal end of atrial/SVC lead 12 is bifurcated connection 21, which connects electrodes 18, 19 and 20 to circuitry within PCD device 10. Electrodes 18 and 19 are used to deliver atrial ATP pulses and for sensing atrial depolarizations or P-waves, while electrode 20 is used for delivering defibrillation or cardioversion shocks.

Coronary sinus lead 13 includes elongated coiled defibrillation electrode 22. Defibrillation electrode 22, illustrated in FIG. 1 as a broken line, is located within the coronary sinus and great vein of the heart. At the proximal end of coronary sinus lead 13 is connector plug 23, which connects defibrillation electrode 22 to circuitry within PCD device 10.

Other lead configurations and electrode locations may be substituted for the lead set illustrated. For example, in a two lead system, atrial defibrillation and sensing electrodes might be added to either coronary sinus lead 13 or right ventricular lead 11 instead of being located on separate atrial lead 12. In any of the configurations, all leads are connected to circuitry within PCD device 10, which controls delivery of ATP pulses and cardioversion shocks to selected electrodes, and processes depolarizations sensed by the electrodes.

For the sake of simplicity, electrode 15 located at the distal end of right ventricular lead 11 is used to illustrate delivery of ATP therapy throughout this description, although any of the electrodes discussed above are capable of providing ATP therapy. ATP therapy delivered by electrode 15 may be used to treat ventricular as well as atrial tachyarrhythmia, although it is usually preferable to apply ATP therapy from an electrode located in the chamber of origin of the tachyarrhythmia.

Figure 2:
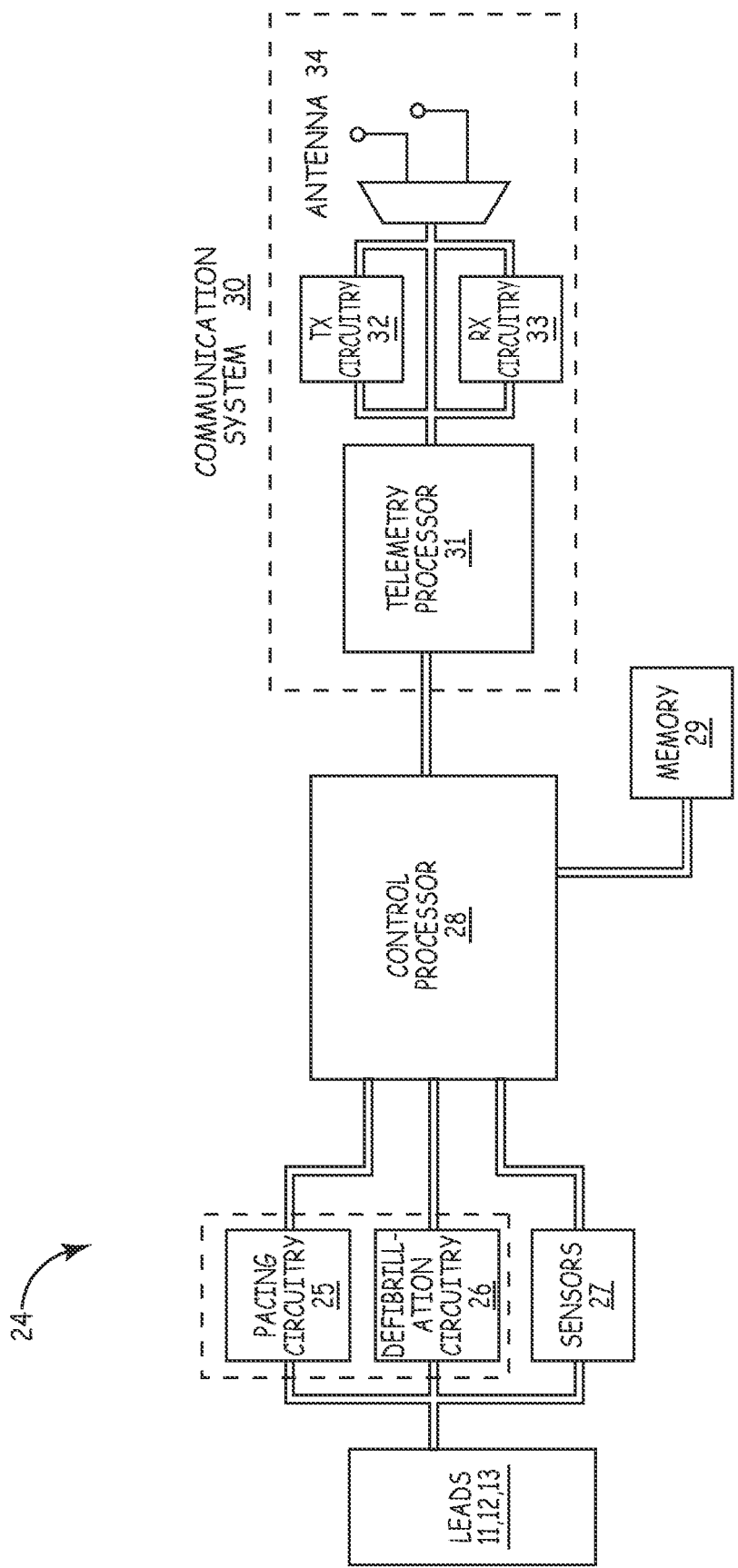
FIG. 2 is a functional block diagram of circuitry located within the pacemaker/cardioverter/defibrillator of FIG. 1.

FIG. 2 shows a simplified functional block diagram of circuitry 24 located within PCD device 10. Circuitry 24 includes pacing circuitry 25, defibrillation circuitry 26, sensor circuitry 27, control processor 28, memory 29, and communication system 30. Leads 11, 12 and 13 are each connected to pacing circuitry 25, defibrillation circuitry 26 and sensor circuitry 27. This is because each lead (and in turn individual electrodes associated with each lead) may be used in multiple capacities to sense depolarizations, deliver antitachycardia pacing pulses, and deliver defibrillation or cardioversion shocks. Control processor 28 receives input through sensor circuitry 27 from leads 11, 12 and 13 concerning depolarizations sensed throughout the heart by the number of electrodes connected to leads 11, 12 and 13. Based on input received from sensor circuitry 27, control processor 28 performs calculations to determine the proper course of action, which may include providing ATP therapy to one or more electrodes through pacing circuitry 25, providing defibrillation or cardioversion shocks to one or more electrodes through defibrillation circuitry 26, or providing no treatment at all. Control processor 28 stores selected data to memory 29, and retrieves stored data from memory 29 as necessary. Communication system 30 includes telemetry processor 31, transmission circuitry 32, receiving circuitry 33, and antenna 34. Communication system 30 allows communication between PCD device 10 and devices external to the patient.

Figure 3:
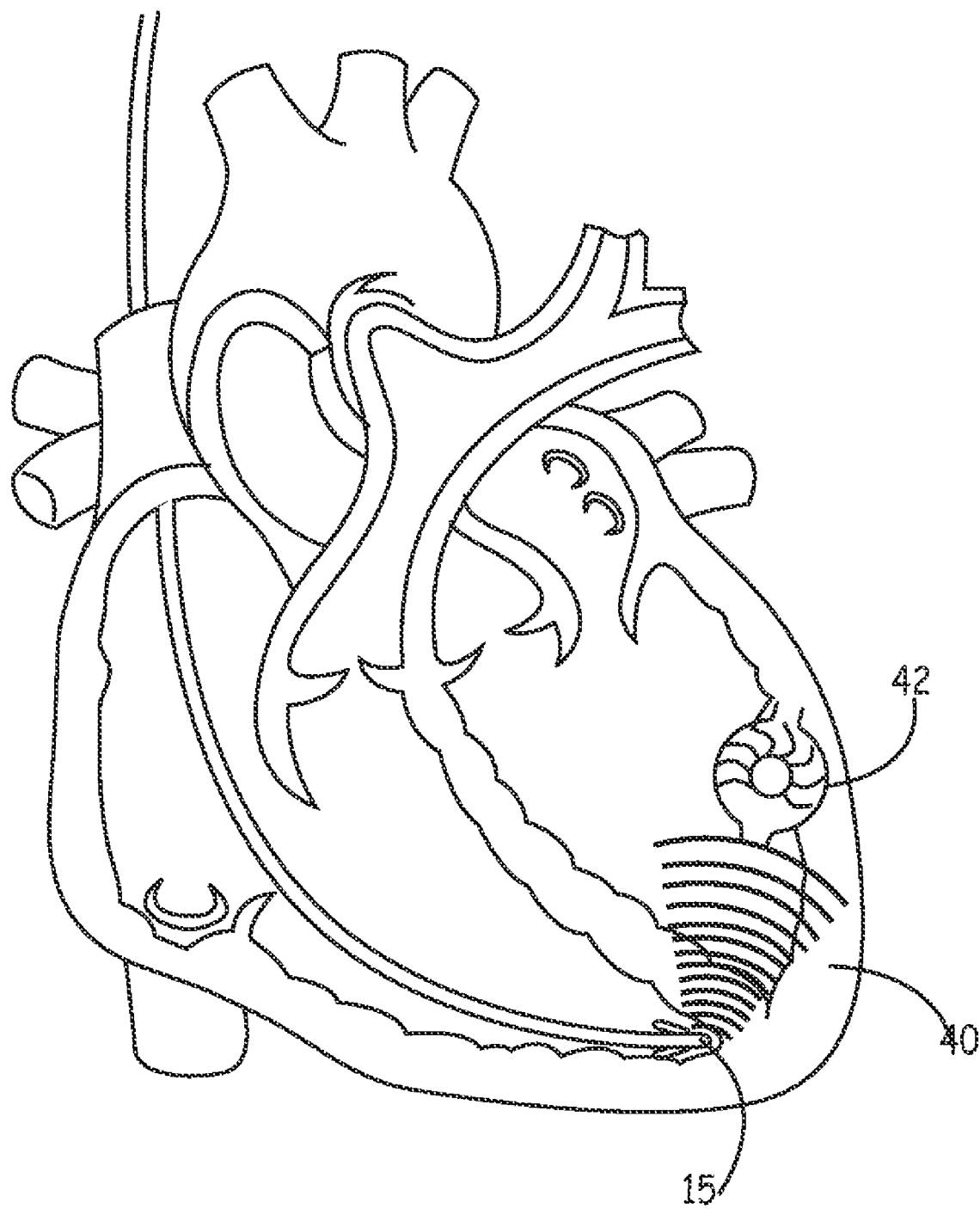
FIG. 3 is a simplified schematic view of delivery of a sequence of ATP pulses to electrode (as shown in FIG. 1) in response to a device detecting a tachycardia event caused by a reentrant tachycardia circuit.

FIG. 3 is a simplified schematic view of PCD device 10 (not shown) delivering a sequence of ATP pulses 40 to electrode 15 (as shown in FIG. 1) in response to detection of a tachycardia event caused by reentrant tachycardia circuit 42. ATP pulses 40 delivered to electrode 15 radiate outward from electrode 15 towards reentrant tachycardia circuit 42. FIGS. 4A-4E show the propagation of ATP pulses 40 in greater detail.

Figure 4B:
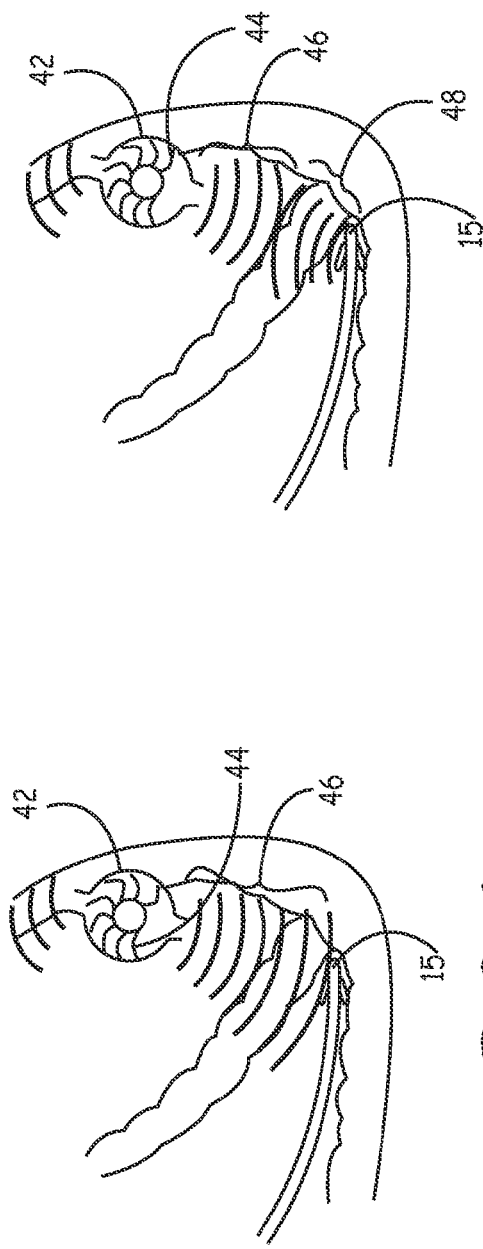
Figure 4B:
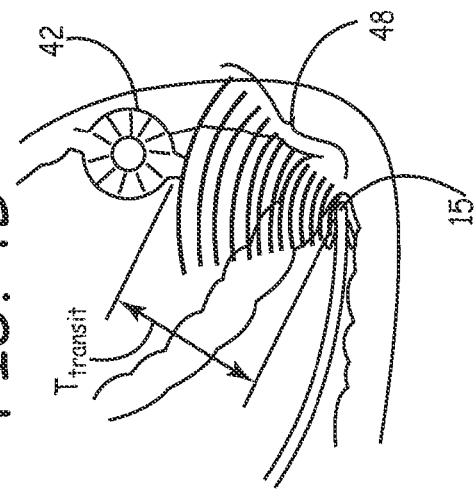

FIGS. 4A-4E are schematic illustrations of termination of a reentrant tachycardia using ATP therapy. FIG. 4A shows reentrant tachycardia circuit 42 and reentrant wavefront 44 circling around circuit 42. As reentrant wavefront 44 propagates around reentrant tachycardia circuit 42, a component of reentrant wavefront 44 also radiates outward away from reentrant circuit 42, shown as outward radiating reentrant wavefronts 46. Reentrant wavefronts 46 radiating away from reentrant circuit 42 are sensed by electrode 15, which is utilized by PCD device 10 to determine the presence of a tachycardia event. The tachycardia cycle length (TCL) is a measured interval of time between successive depolarization wavefronts sensed by an electrode during a tachycardia event. While a tachycardia event, which is identified in response to a multiple number of intervals having corresponding cycle lengths less than a predetermined threshold, and may therefore consist of a multiple number of different cycle lengths, the tachycardia event can be assigned a tachycardia cycle length based on a single cycle length measurement associated with one of the multiple cycle lengths, or on an average of the cycle lengths associated with several successive intervals.

As illustrated in FIG. 4B, PCD device 10 responds to the sensed tachycardia event by delivering ATP therapy, which consists of a number of ATP pulses (a regimen) 48 delivered to electrode 15. ATP pulses 48 radiate away from electrode 15 in all directions, including towards reentrant circuit 42, and collide with outward radiating reentrant wavefronts 46 radiating away from reentrant circuit 42, causing a cancellation of both outward radiating reentrant wavefronts 46 and ATP pulse 48. By delivering ATP pulses 48 at a rate faster than the pace of outward radiating reentrant wavefronts 46, collisions between ATP pulses 48 and outward radiating reentrant wavefronts 46 occur further and further from electrode 15 and closer and closer to reentrant circuit 42.

Figure 4D:
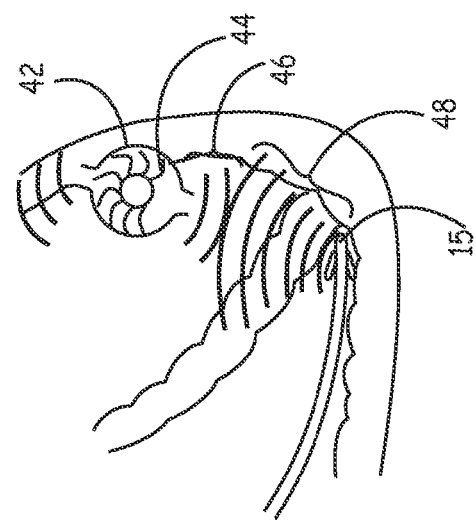

FIGS. 4C and 4D illustrate this point, as ATP pulses 48 are provided at a rate faster than the tachycardia (and therefore the pace of incoming reentrant wavefronts 46) such that successive ATP pulses 48 in the regimen progress closer and closer to reentrant circuit 42. This process of progressing closer and closer to reentrant circuit 42 with each successive ATP pulse 48 is known as "peelback."

Figure 4E:
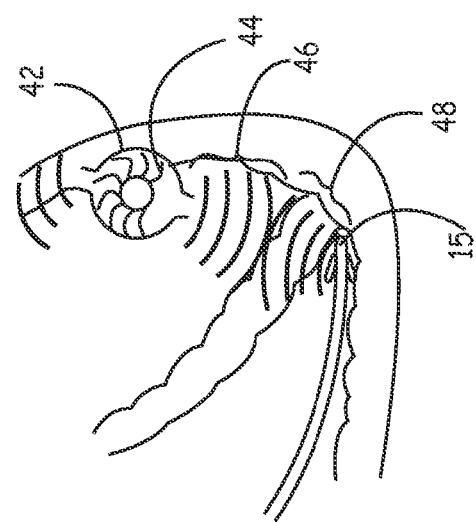

In FIG. 4E, ATP pulses 48 are delivered at a rate greater than the rate of the tachycardia event that enables ATP pulses 48 to reach and enter reentrant circuit 42. With the proper timing of the ATP pulses 48, excitable cardiac tissue within reentrant circuit 42 is depolarized, thus blocking circulating of reentrant wavefront 44 within reentrant circuit 42 and terminating the tachycardia event. As described below, during delivery of an antitachycardia pacing regimen, the present invention takes into account a transit time ($t_{transit}$), which is the amount of time for a pulse to travel from the pacing site (e.g. electrode 15) to reentrant circuit 42. Although the transit time $t_{transit}$ could also be expressed as a distance, it is easier to think about the distance between the pacing site and reentrant circuit 42 in terms of time, as timing is directly controlled by the system, and because other values such as prematurity, described below, are expressed in time. The present invention adjusts the delivery of an ATP therapy by determining a transit time associated with the sensed tachycardia event and, based on the determined transit time, determining a number of pulses required for the ATP therapy to reach the associated reentrant circuit, described below in detail.

FIGS. 4A-4E illustrate the basics of how ATP therapy terminates reentrant tachycardias. In order to be effective, the ATP therapy regimen must succeed in two objectives. The first objective is to advance the wavefront created by ATP pulses 48 all the way to the location of reentrant circuit 42. In order to move each successive collision between ATP pulses 48 and outward radiating reentrant wavefronts 46 closer and closer to reentrant circuit 42, each ATP pulse provided in a given regimen is provided at a rate, known as the ATP cycle length, that is faster than the rate of the tachycardia. The ATP cycle length is defined for each ATP pulse in a given regimen as the interval of time from either the last sensed depolarization wavefront (for the first pace of a therapy regimen), or the previous delivered ATP pulse, until the delivery of the next ATP pulse.

The second objective is to eliminate the excitability in reentrant circuit 42 so the reentry process can no longer occur. This is a function of advancing the rate of the tachycardia within reentrant circuit 42 to a rate that cannot be sustained by the circuit 42, and is therefore related to the fastest pacing rate to reach reentrant circuit 42.

Figure 5:
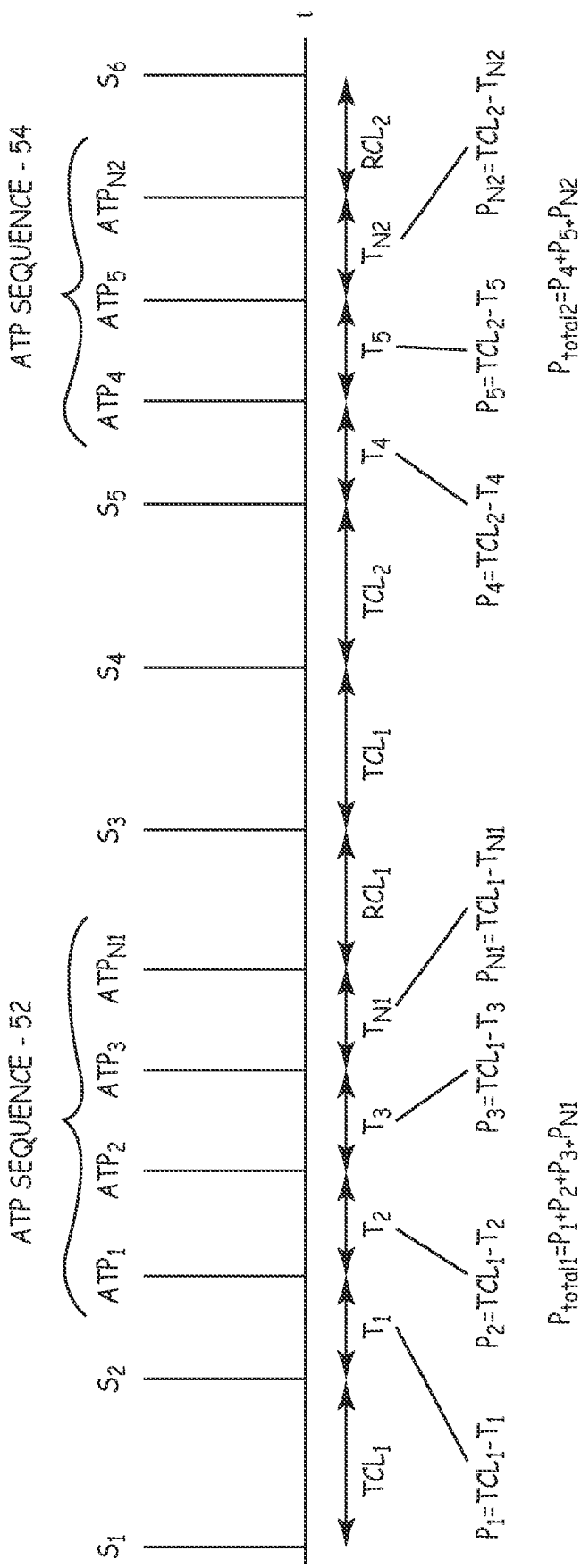
FIG. 5 is a graphical representation of delivery of an anti-tachycardia pacing therapy according to an embodiment of the present invention.

FIG. 5 is a graphical representation of delivery of an antitachycardia pacing therapy according to an embodiment of the present invention. Depolarizations or signals sensed by electrode 15 are labeled $S_1$, $S_2$, $S_3$, $S_4$, $S_5$, and $S_6$. ATP pulses in a first ATP regimen 52 delivered by electrode 15 are labeled $ATP_1$, $ATP_2$, $ATP_3$ . . . $ATP_{N1}$, with $ATP_{N1}$ representing the last pacing pulse provided in the first regimen. ATP pulses in a second ATP regimen 54 delivered by electrode 15 are labeled $ATP_5$, $ATP_6$ . . . $ATP_{N2}$, with $ATP_{N2}$ representing the last pacing pulse provided in the second regimen. The second ATP regimen 54 is only provided if the device 10 determines that the first ATP regimen 52 failed to terminate the tachycardia.

The time interval between successive sensed signals $S_1$ and $S_2$ is the tachycardia cycle length ($TCL_1$), and alerts PCD device 10 to the ongoing tachycardia. $TCL_1$ is stored by PCD device 10 for a number of reasons discussed below. In response to the detected tachycardia event, PCD device 10 generates ATP regimen 52 including ATP pulses $ATP_1$, $ATP_2$, $ATP_3$ . . . $ATP_{N1}$, and delivers ATP regimen 52 to an electrode (in this example, electrode 15), according to the embodiments described below.

According to the present invention, a prematurity of each ATP pulse ($P_i$), corresponding to how much faster the rate at which the ATP pulse is delivered relative to the rate of the tachycardia event, is determined and subsequently utilized to determine the number of pacing pulses to be delivered, described below. Stated differently, the prematurity of the ATP pulse ($P_i$) corresponds to how much shorter the cycle length of the ATP pulse ($P_i$) is relative to the tachycardia cycle length TCL. Therefore, the prematurity of the ATP pulse ($P_i$) can be defined as the difference between that pulse's ATP cycle length ($T_i$) and the tachycardia cycle length TCL, as set forth in Equation 1.

$$P_i = TCL - T_i \qquad \text{Equation 1}$$

The total prematurity of a pacing regimen ($P_{TOTAL}$) is defined as the sum of the individual prematurities for each ATP pulse $P_i$ $$\left( \text{i.e., } P_{TOTAL} = \sum_{i=1}^{n} P_i \right).$$

From this definition, it can be seen that $P_{TOTAL}$ describes the effects of both the ATP cycle lengths and the number of ATP pulses delivered.

A "burst" ATP regimen is defined as an ATP regimen where all of the ATP cycle lengths $T_i$ are equal, resulting in all corresponding prematurities $P_i$ being equal per Equation 1. For burst ATP regimens, prematurity of each pulse is denoted simply as prematurity P. This is a common and simple form of ATP therapy that is instructive because it gives a total prematurity $P_{TOTAL}$ equal to the number of pulses n in an ATP regimen times the prematurity P associated with each ATP pulse (i.e., n*P).

According to the present invention, ATP pacing regimen 52 is defined by prematurity $P_i$ associated with each ATP pulse and the number of pulses n included in the regimen. In the first ATP regimen 52, $ATP_1$ is delivered a time $T_1$ after depolarization $S_2$ is sensed by electrode 15 (i.e., ATP cycle length of pulse $ATP_1$ is $T_1$). The prematurity associated with the first pulse $ATP_1$ is shown in FIG. 5 as $P_1 = TCL_1 - T_1$. For example, if the tachycardia cycle length TCL was measured to be 400 ms, and $ATP_1$ is provided 350 ms after $S_2$, then prematurity $P_1$ would be equal to 50 ms, meaning that $ATP_1$ is provided 50 ms before the next reentrant wavefront would have been sensed by electrode 15. The next pulse $ATP_2$ is delivered a time $T_2$ following delivery of the previous pulse $ATP_1$ (i.e., ATP cycle length of pulse $ATP_2$ is time $T_2$). The prematurity associated with $ATP_2$ is $P_2 = TCL_1 - T_2$. Likewise, the prematurity associated with $ATP_3$ delivered a time $T_3$ after $ATP_2$ is $P_3 = TCL_1 - T_3$.

According to the present invention, in order to calculate the total prematurity $P_{total}$ associated with ATP regimen 52, each individual prematurity ($P_1$, $P_2$, $P_3$ . . . $P_{N1}$) is summed. As discussed above, for the sake of simplicity, the remainder of ATP pacing regimens discussed in FIG. 5 are burst pacing regimens, (i.e., constant ATP cycle length, $T_1 = T_2 = T_3 = T_n$) making associated prematurities $P_i$ equal and $P_{TOTAL}$ equivalent to n*P. In other embodiments, different ATP pacing regimens are used (for example, ramp ATP in which the time between successive ATP pulses is shortened), and $P_{TOTAL}$ has to be calculated as a sum of each prematurity $P_i$, making operations such as selection of number of pacing pulses n more involved, but with the same principles still applying.

After delivery of the last ATP pulse ($ATP_{N1}$) in ATP regimen 52, electrode 15 is used to sense the next depolarization $S_3$. The time between delivery of last ATP pulse $ATP_{N1}$ and the sensing of depolarization $S_3$ is return cycle length $RCL_1$ resulting subsequent to delivery of ATP regimen 52. In the present invention, return cycle length RCL is used to provide information regarding the effect of the preceding train of ATP pulses on reentrant tachycardia circuit 42 (shown in FIGS. 4A-4E), this information then guides subsequent therapies, as will be described below. Device 10 stores and processes return cycle length $RCL_1$, and based on a number of calculations employing return cycle length RCL, device 10 customizes subsequent ATP regimen 54. It should be noted that in other embodiments, more than one electrode may be used to sense depolarizations and deliver ATP pulses. If more than one electrode is used, then time differences caused by the physical separation of the two electrodes must be taken into account when analyzing return cycle length.

Assuming ATP regimen 52 did not terminate the reentrant tachycardia, determined by monitoring the time interval between subsequent depolarizations ($S_3$ and $S_4$ for example), then PCD device 10 delivers ATP regimen 54 to electrode 15. Based on the return cycle length $RCL_1$ measured following ATP regimen 52, PCD device 10 customizes ATP regimen 54 to improve the likelihood that ATP regimen 54 will terminate the tachycardia. Like ATP regimen 52, to calculate the prematurity associated with ATP regimen 54, the prematurity associated with each ATP pulse ($P_4 = TCL_2 - ATP_5$, $P_5 = TCL_2 -$ $ATP_6 \ldots P_N=TCL_2-ATP_{N2}$) must be taken into account. The delivery of ATP regimen 52 has no effect on the calculation of the prematurity associated with ATP regimen 54, all therapy regimens operate nearly independent as far as effects on tachycardia circuit 42. After delivery of the final pulse $ATP_{N2}$ of the subsequent ATP regimen, device 10 measures the time until the next sensed depolarization $S_6$ to determine the return cycle length ($RCL_2$). The process is repeated, with a subsequent pacing regimen (not shown) provided by PCD device 10 depending on whether the tachycardia has been terminated and on the measurement of previous return cycle lengths $RCL_2$, and so forth.

According to the present invention, following delivery of ATP regimen 52 and ATP regimens in general, there are five possible scenarios that result from ATP application:
1. Successful termination of the tachycardia;
2. Displacement of tachycardia circuit (i.e., termination of the original tachycardia but initiation of a new tachycardia);
3. Failed termination because of a failure to consistently capture tissue around the stimulation electrode (e.g., electrode 15);
4. Failed termination because of failure to complete peelback
5. Failed termination because of failure to extinguish reentrant circuit excitability when circuit was reached (also know as continuous resetting of reentrant circuit 64 or entrainment).

In the present invention, the methods for detecting which of these possible cases actually occurred leads to the tailoring of subsequent therapy. Termination of reentrant tachycardia is detected by measuring a return to a normal beating pattern of the heart. In this scenario, no further ATP regimens are required. Displacement is a scenario equivalent to the original initiation of a new tachycardia. For the remaining scenarios of ATP failure, device 10 uses circuitry to analyze the return cycle length $RCL_1$ to determine which of the remaining three scenarios has occurred following delivery of ATP regimen 52. By determining which scenario has occurred, device 10 is able to customize subsequent pacing regimens to better terminate the reentrant tachycardia.

Figure 6:
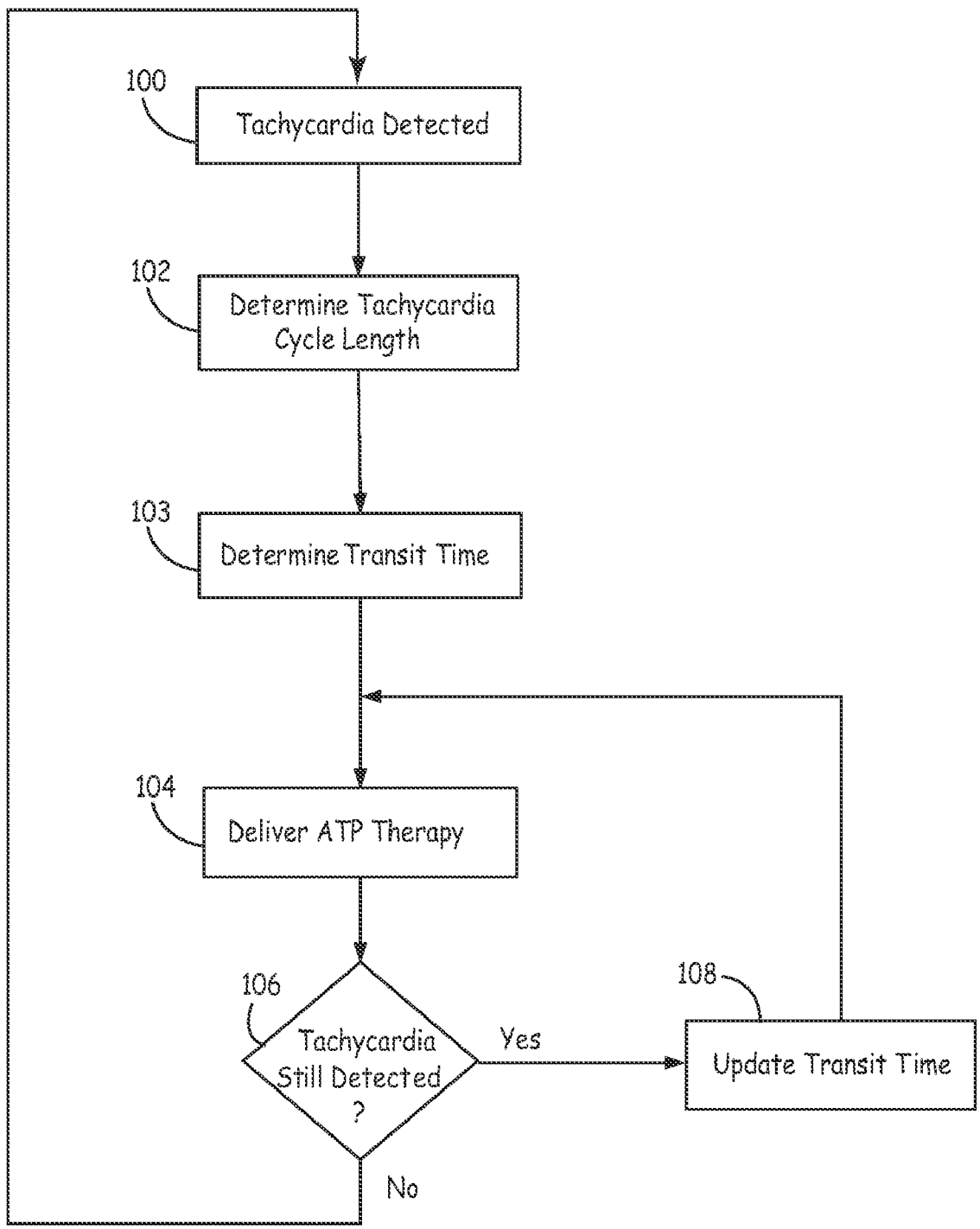
FIG. 6 is a flowchart of delivery of anti-tachycardia pacing therapy according to an embodiment of the present invention.

FIG. 6 is a flowchart of delivery of anti-tachycardia pacing therapy according to an embodiment of the present invention. As illustrated in FIG. 6, according to an embodiment of the present invention, device 10 determines whether a tachycardia event has been detected, Block 100, in response to a measured time interval between successive depolarizations sensed by electrode 15 being less than a predetermined threshold value, for example. Once a tachycardia event is determined to be occurring, Block 100, the device 10 determines an initial tachycardia cycle length ($TCL_{initial}$), Block 102, based on a mean time interval between successive depolarizations sensed by electrode 15. The device 10 then determines a transit time $t_{transit}$, Block 103, associated with the detected tachycardia event. Initially, the transit time $t_{transit}$ is set as an estimate of a maximum time required to depolarize any point in the ventricle from electrode 15. For example, the initial transit time $t_{tansit}$ is selected to be around 180 ms. In other embodiments, the initial estimate of the transit time $t_{transit}$ is selected based on past $t_{transit}$ times recorded by PCD device 10 or a population average value for the transit time $t_{transit}$. In other embodiments, the transit time $t_{transit}$ is selected based on a comparison of measured properties of the current tachycardia with measured values of previous tachycardias with a known or estimated transit time $t_{transit}$. Tachycardias with similar measured properties may be indicative of similarly located reentrant circuits. Measured properties of tachycardias include tachycardia cycle length, as well as tachycardia complex morphology.

Once the initial transit time transit time $t_{transit}$ is determined, the minimum number of pacing pulses required to have a therapy extend to the transit time $t_{transit}$ is calculated. This is done according to the concept of total prematurity. The minimum number of pulses is that for which the total prmaturity of the pulses reaches or exceeds twice the transit time $t_{transit}$. This combination of pacing pulses is then delivered, Block 104. It is important to note that using the concept of total prematurity, either the rate of ATP pulses or the number of ATP pulses, or both, can be manipulated to achieve a sufficiently large total prematurity.

Once the initial pacing pulses have been delivered in Block 104, a determination is made as to whether the tachycardia event has been terminated, Block 106. If the tachycardia event has been terminated, No in Block 106, the process waits until a tachycardia event is again detected Block 100. If the tachycardia event has not been terminated, Yes in Block 106, the transit time $t_{transit}$ is updated, Block 108, as described below, and a next pacing therapy regimen that utilizes the current updated transit time $t_{transit}$ is delivered Block 104. The process continues with a determination in Block 106 as to whether the tachycardia event has been terminated in response to the next delivered pacing therapy regimen. In this way, the present invention varies the delivered pacing therapy by varying the transit time $t_{tansit}$ after each failed therapy regimen, and modifying the subsequent ATP therapy regimen to extend to the newly determined transit time $t_{transit}$.

As described above in reference to FIG. 5, the return cycle length (RCL) is defined as the time interval from the delivery of the final ATP pulse of a regimen to an electrode (i.e., the pacing site) until the first depolarization wavefront is sensed at the pacing site. As illustrated in FIG. 4E, since a path of an ATP pulse that successfully reaches reentrant circuit 42 travels for transit time $t_{tansit}$, and enters and entrains reentrant circuit 42 (taking an amount of time equal to the tachycardia cycle length TCL), the return cycle length RCL can be expressed as a sum of the tachycardia cycle length and the transit time $t_{transit}$ as set forth in the following Equation 2:

$$RCL = TCL + 2*t_{transit} \quad \text{Equation 2}$$

Solving for the transit time $t_{transit}$ results in the following Equation 3:

$$t_{transit} = \frac{RCL - TCL}{2} \quad \text{Equation 3}$$

According to the present invention, since both the return cycle length RCL and the tachycardia cycle length TCL are known subsequent to the delivery of the initial pacing regimen, the device 10 varies the next pacing therapy that is subsequently delivered by updating the transit time $t_{transit}$ in Block 108 using Equation 3, and setting the current transit time $t_{transit}$ equal to the updated transit time $t_{transit}$ so that the next pacing regimen is delivered in Block 104 using the updated transit time $t_{transit}$. In particular, for example, the updated transit time $t_{transit}$ will result in the predetermined number of pacing pulses (n) being reduced, as will be described below.

Figure 7:
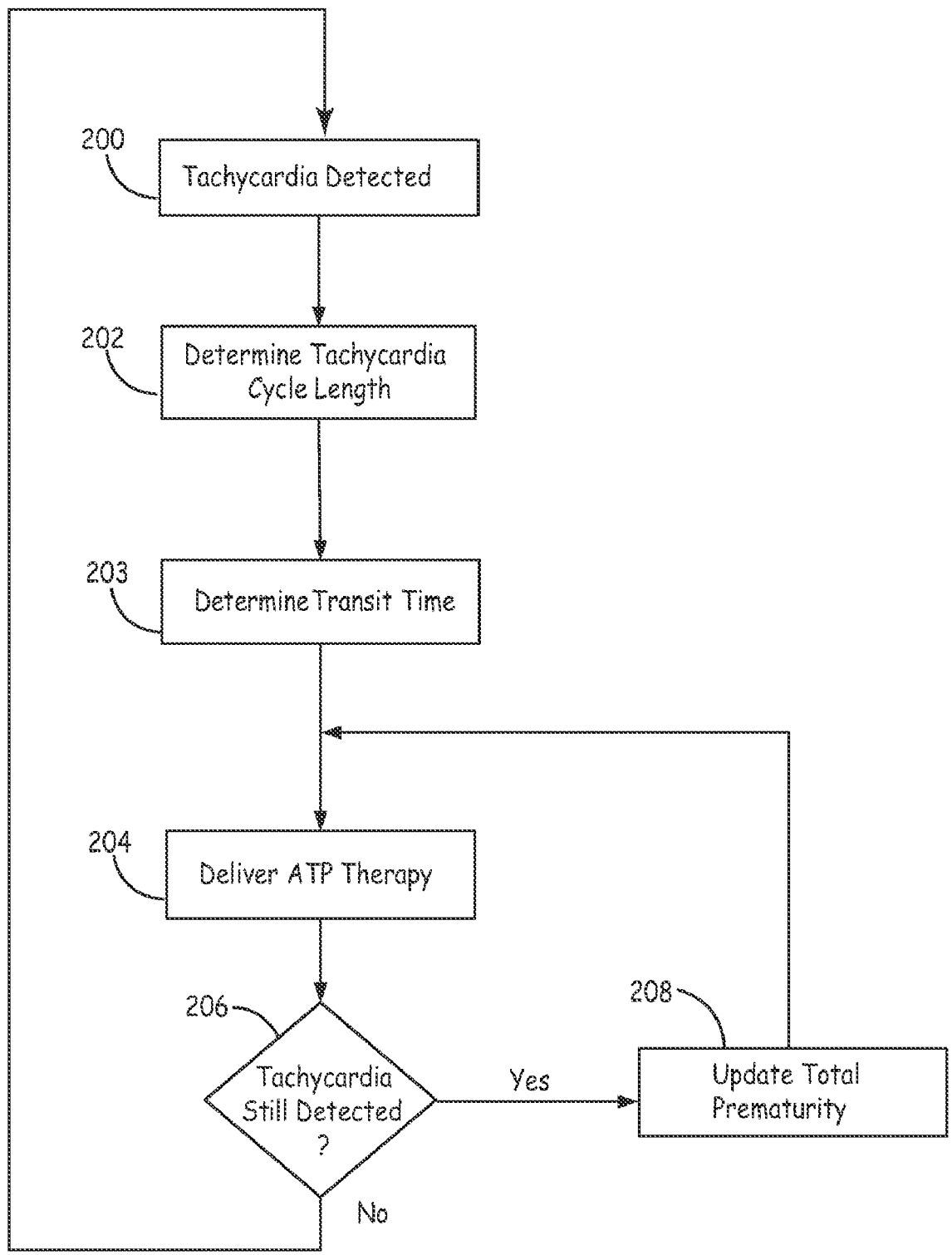
FIG. 7 is a flowchart of delivery of anti-tachycardia pacing therapy according to an embodiment of the present invention.

FIG. 7 is a flowchart of delivery of anti-tachycardia pacing therapy according to an embodiment of the present invention. As illustrated in FIG. 7, according to an embodiment of the present invention, device 10 determines whether a tachycardia event has been detected, Block 200, in response to a measured time interval between successive depolarizations sensed by electrode 15 being less than a predetermined threshold value, for example. Once a tachycardia event is determined to be occurring, the device 10 determines an initial tachycardia cycle length ($TCL_{initial}$), Block 202, based on a mean time interval between successive depolarizations sensed by electrode 15. The device 10 then determines a transit time $t_{transit}$, Block 203, associated with the detected tachycardia event. Initially, the transit time $t_{transit}$ is set as an estimate of a maximum time required to depolarize any point in the ventricle from electrode 15. For example, the initial transit time $t_{tansit}$ is selected to be around 180 ms. In other embodiments, the initial estimate of the transit time $t_{transit}$ is selected based on past $t_{transit}$ times recorded by PCD device 10 or a population average value for the transit time $t_{transit}$. In other embodiments, the transit time $t_{transit}$ is selected based on a comparison of measured properties of the current tachycardia with measured values of previous tachycardias with known or estimated $t_{transit}$ times. Tachycardias with similar measured properties may be indicative of similarly located reentrant circuits. Measured properties of tachycardias include tachycardia cycle length, as well as tachycardia complex morphology.

Once the initial transit time transit time $t_{transit}$ is determined, the minimum number of pacing pulses required to have a therapy extend to the transit time $t_{transit}$ is calculated. This is done according to the concept of total prematurity. The minimum number of pulses is that for which the total prmaturity of the pulses reaches or exceeds twice the transit time $t_{transit}$. This combination of pacing pulses is then delivered, Block 204. It is important to note that using the concept of total prematurity, either the rate of ATP pulses or the number of ATP pulses, or both, can be manipulated to achieve a sufficiently large total prematurity.

Once the initial pacing pulses have been delivered in Block 204, a determination is made as to whether the tachycardia event has been terminated, Block 206. If the tachycardia event has been terminated, No in Block 206, the process waits until a tachycardia event is again detected, Block 200. If the tachycardia event has not been terminated, No in Block 204, a total prematurity $P_{TOTAL}$ is updated, Block 206, and a next pacing therapy regimen that utilizes the current updated total prematurity $P_{TOTAL}$ is delivered and the process continues with the determination in Block 104 as to whether the tachycardia event has been terminated in response to the next delivered pacing therapy regimen. According to the present invention, the total prematurity $P_{TOTAL}$ is updated for the next delivered ATP regimen in Block 208 by either increasing one or more of the individual prematurities $P_j$, or by increasing the number of pulses delivered, as described below. In this way, the present invention varies the delivered pacing therapy by varying the total prematurity $P_{TOTAL}$ after each failed therapy regimen.

Figure 8:
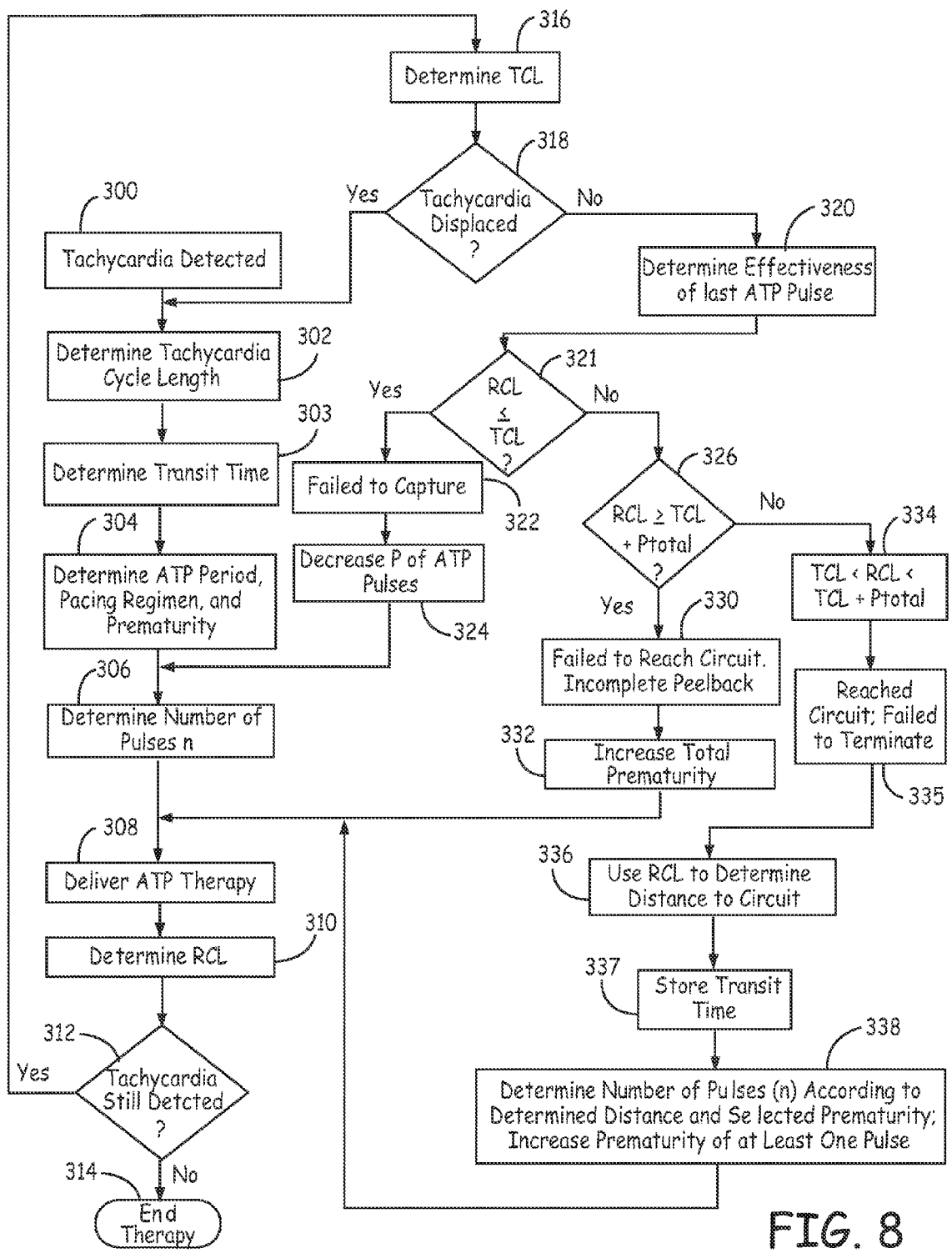
FIG. 8 is a flowchart of delivery of anti-tachycardia pacing therapy according to an embodiment of the present invention.

FIG. 8 is a flowchart of delivery of anti-tachycardia pacing therapy according to an embodiment of the present invention. In order to illustrate specific application of the methods for tailoring therapy, an example of controlling burst ATP will be carried through the description of FIG. 8. In this embodiment, electrode 15 is used to detect electrical pulses for device 10, as well as for delivering ATP pulses from device 10.

As illustrated in FIG. 8, according to an embodiment of the present invention, device 10 determines that a tachycardia event has been detected, Block 300, in response to a measured time interval between successive depolarizations sensed by electrode 15 being less than a predetermined threshold value, for example. Once a tachycardia event is determined to be occurring, device 10 determines an initial tachycardia cycle length ($TCL_{initial}$), Block 302, based on a mean time interval between successive depolarizations sensed by electrode 15. The device 10 then determines a transit time $t_{transit}$, Block 303, associated with the detected tachycardia event. Initially, the transit time $t_{transit}$ is set as an estimate of a maximum time required to depolarize any point in the ventricle from electrode 15. For example, the initial transit time $t_{tansit}$ is selected to be around 180 ms. In other embodiments, the initial estimate of the transit time $t_{transit}$ is selected based on past $t_{transit}$ times recorded by PCD device 10 or a population average value for the transit time $t_{transit}$. In other embodiments, the transit time $t_{transit}$ is selected based on a comparison of measured properties of the current tachycardia with measured values of previous tachycardias with known or estimated $t_{transit}$ times. Tachycardias with similar measured properties may be indicative of similarly located reentrant circuits. Measured properties of tachycardias include tachycardia cycle length, as well as tachycardia complex morphology.

Device 10 also determines an initial ATP pulse period ($T_1$), based on the initial return cycle length $TCL_{initial}$, and the type of pacing scheme to be utilized for determining the ATP pulse period $T_i$ of the subsequent pulses in the initial ATP regimen, Block 304. For example, a burst, a ramp, or some other desired pacing scheme may be selected. A prematurity associated with the initial ATP pulse period $T_1$ is also determined in Block 304 using Equation 1. Selecting the initial ATP pulse period $T_i$ has the effect of defining prematurity $P_i$ associated with each ATP pulse. For example, if the initial tachycardia cycle length $TCL_{initial}$ is measured to be 400 ms, and ATP pulse period $T_1$ is set at 360 ms (80% of $TCL_{initial}$), then the prematurity $P_1$ ($TCL_{initial}-T_1$) associated with ATP period $T_1$ is 40 ms.

Device then determines the number of ATP pulses n that are required to be included in the pulse regimen, Block 306, based on the choice of ATP regimen pacing scheme, to ensure peelback is completed and the delivered pacing pulse wavefronts of the pacing regimen reach reentrant circuit 42. This is done by ensuring the sequence of pulses is constructed such that total prematurity $P_{TOTAL}$ is at least twice time $t_{transit}$. For the burst ATP example, with the initial estimated transit time $t_{transit}$ of 180 ms, PCD device 10 uses the following Equation 4 in order to determine the expected number of pulses n needed to reach reentrant tachycardia circuit 42. If time $t_{transit}$ is known from RCL analysis for the tachycardia, then this known value is used in subsequent returns to Step 306, as described below.

$$n = \frac{P_{TOTAL}}{P} = \left[\frac{(2*t_{transit})}{P}\right] \qquad \text{Equation 4}$$

Therefore, in this burst pacing example, if the tachycardia cycle length TCL is equal to 400 ms, and ATP pulse period $T_1$ is set at 360 ms (80% of $TCL_{initial}$), so that the prematurity $P_1$ ($TCL_{initial}-T_1$) associated with ATP period $T_1$ is 40 ms, the number of pulses n is determined to be approximately equal to 9 (n=360/40).

When a burst pacing scheme is utilized, calculation of the number of pulse n is simplified, since all of the associated ATP pulses periods $T_i$ of the delivered pacing therapy are equal and therefore all of the prematurities $P_i$ are equal. Therefore, the calculation of the prematurity P in Equation 4 involves a single calculation. If a ramp ATP regimen is utilized, example, the device 10 determines the number of pulses n required by calculating multiple prematurities in order to determine when the prematurity associated with ramped pulses initially becomes greater than or equal to twice the initial estimated transit time $t_{transit}$. For example, assuming the initial return cycle length $TCL_{initial}$ is determined to be 400 ms in Block 302, and the pulse pacing scheme is a ramp scheme in which the initial ATP pulse period $T_1$ is set at 360 ms (80% of $TCL_{initial}$) and the pulse rate is increased by 10 ms for each subsequently delivered pacing pulse, the prematurity $P_1$ of initial pacing pulse $T_1$ is 40 ms, which is not greater than or equal to twice the initial estimated transit time $t_{transit}$ (360 ms), the prematurity $P_2$ of the next pacing pulse $T_2$ is 90 ms (40+(40+10)), the prematurity $P_3$ of the next pacing pulse $T_3$ is 150 ms, the prematurity $P_4$ of the next pacing pulse $T_4$ is 220 ms, the prematurity $P_5$ of the next pacing pulse $T_5$ is 300 ms, and the prematurity $P_6$ of the next pacing pulse $T_6$ is 390 ms. Therefore, the number of pacing pulses required in such a ramp pacing scheme is approximately 6, since it is at the $6^{th}$ pacing pulse $T_6$ that the prematurity associated with ramped pulses is first greater than or equal to twice the initial estimated transit time $t_{transit}$.

Once the number of pacing pulses n has been determined, device 10 delivers the pacing regimen to electrode 15, Block 308, using the determined pulse pacing scheme, ATP pacing periods $T_i$, and the number of pulses n.

Once the pacing regimen has been delivered, device 10 measures and stores a return cycle length RCL detected by electrode 15, Block 310. Return cycle length RCL is the measured time between the last ATP pulse delivered by device 10 to electrode 15 and the next depolarization sensed by electrode 15 as shown in FIG. 5.

At approximately the same time, device 10 measures time intervals between successive depolarizations sensed by electrode 15 to determine if the tachycardia event has been terminated, Block 312. If device 10 determines the tachycardia event has been terminated, No in Block 312, then ATP treatment is terminated, Block 314.

If tachycardia has not been terminated, Yes in Block 312, treatment continues with device 10 measuring the current tachycardia cycle length $TCL_{current}$, Block 316. Based on the determined current tachycardia cycle length $TCL_{current}$, device 10 determines whether the reentrant circuit 42 associated with the initially detected tachycardia event has been displaced as a result of the delivered ATP regimen, Block 318. According to an embodiment of the present invention, device 10 determines whether the tachycardia event has been displaced by detecting whether a substantial alteration in the characteristics of the tachycardia has occurred. For example, according to one embodiment device 10 compares the current tachycardia cycle length $TCL_{current}$ with the initial tachycardia cycle length $TCL_{initial}$. If the difference between the current tachycardia cycle length $TCL_{current}$ and the initial tachycardia cycle length $TCL_{initial}$ is greater than a predetermined displacement threshold, device 10 determines that reentrant circuit 42 has been displaced, and therefore the current detected tachycardia event is associated with a new reentrant circuit in a new location. According to an embodiment of the present invention, displacement threshold is set as 50 ms.

If the tachycardia event has been displaced, Yes in Block 318, the return cycle length RCL cannot be used to provide complete information about the new reentrant circuit location and the situation becomes functionally identical to the situation prior to the first ATP regimen where the transit time $t_{transit}$ must again be estimated, Block 303. In other embodiments, a change in the properties of the depolarization signal sensed by an electrode is used alone or in conjunction with a change in the current tachycardia cycle length $TCL_{current}$ to detect displacement (e.g., tachycardia complex morphology). For each discovery of a new circuit, the functional status returns to that of initial detection of a tachycardia, and proceeds from Block 303.

Once device 10 determines that reentrant circuit 42 has not been displaced, No in Block 318, device 10 uses the return cycle length RCL, Block 320, to determine the effectiveness of the previous delivered ATP therapy. Based on the measured return cycle length RCL, device 10 is able to distinguish between three remaining scenarios that are possible following delivery of an ATP pacing regimen: (1) failure to capture, (2) failure to complete peelback, and (3) reset of reentrant circuit but no termination. The following return cycle length RCL relationships (in which $TCL=TCL_{initial}$) identify the scenarios.

| Scenario F1: | $RCL \leq TCL$ | Failure to Capture |
|---|---|---|
| Scenario F2: | $RCL >$ or approximately $= TCL + P_{TOTAL}$ | Incomplete Peelback |
| Scenario F3: | $TCL < RCL < TCL + P_{TOTAL}$ | Reset |

In particular, in order to determine the effectiveness of the delivered ATP therapy, device 10 determines whether the return cycle length RCL is less than or equal to the tachycardia cycle length TCL, prior to the delivery of therapy, Block 321. If the return cycle length RCL is less than or equal to the tachycardia cycle length TCL, Yes in Block 321, the delivered therapy is determined to have failed to capture the tachycardia event, Block 322.

According to the present invention, such a determination of failure to capture Block 321 being detected is indicative that the pacing period of one or more pulses of the prior pacing regimen was likely too fast, preventing cardiac tissue surrounding electrode 15 from recovering from the previous pacing pulse. Therefore, in response to determining that the delivered therapy failed to capture the tachycardia event, Block 322, device 10 changes the ATP pacing therapy by increasing at least one of the ATP pacing periods $T_i$ associated with the next ATP therapy to be subsequently delivered, in order to allow more recovery time for the cardiac tissue. That is, the coupling interval between the pulse that failed to capture and the previous pulse is increased to provide more time for tissue to recover. The result of increasing the at least one of the ATP pacing periods $T_i$ is that the prematurity P of Equation 4 is decreased, Block 324.

According to an embodiment of the present invention, device 10 increases all of the periods $T_i$ when burst pacing is utilized, for example, resulting in all of the associated prematurities $P_i$ being decreased. Since decreasing the prematurities $P_i$ of each of the ATP pulses requires that the number of pulses n delivered must be increased in order to provide the total prematurity $P_{TOTAL}$ necessary to complete peelback, once device 10 determines the delivered ATP therapy failed to capture reentrant circuit 42, device 10 updates the prematurity P, i.e., decreases the prematurity P by increasing the ATP pacing periods $T_i$, Block 324. Device 10 then updates the number of pulse n required in order to reach reentrant circuit 42 using Equation 4 and newly decreased prematurity P, based on the current value of time $t_{transit}$, either using the estimated initial value or using an updated value determined using Equation 3 and the return cycle length RCL determined in Block 310 and the tachycardia cycle length TCL determined in Block 316 from a prior delivered ATP sequence. For the burst example, as ATP period $T_i$ is increased (to prevent a second pacing regimen from failing to capture) the number of pulses required to reach reentrant circuit 42 increases per Equation 4. After selecting a new pacing period $T_i$, resulting in a decrease in prematurity P, Block 324, and determining the number of ATP pulses n required to reach reentrant circuit 42, Block 306, device 10 delivers the new ATP regimen, Block 308.

After delivering the new ATP pulse train, Block 308, device 10 again measures the return cycle length RCL, Block 310, while also measuring successive sensed depolarizations to determine if the tachycardia event has been terminated, Block 312. If the tachycardia event has not been terminated, then device 10 uses the new return cycle length RCL, Block 316, to determine the effect of the latest ATP pulse train on reentrant circuit 42, Block 320, and update the subsequent delivery of ATP therapy based on the determined effect.

If device determines that the return cycle length is not less than or equal to the tachycardia cycle length TCL, No in Block 321, and therefore there was not a failure to capture, device 10 determines whether the return cycle length RCL is greater than or equal to the sum of the tachycardia cycle length TCL and the total prematurity $P_{TOTAL}$, Block 326. If the return cycle length RCL is determined to be greater than the sum of the tachycardia cycle length TCL and the total prematurity $P_{TOTAL}$, Yes in Block 326, the effect of peelback was not complete and therefore the delivered therapy is determined to have failed to reach reentrant circuit 42, Block 330.

If a burst pulse therapy regimen is utilized, for example, each of the individual prematurities are equal, and therefore the return cycle length RCL is determined to be greater than the tachycardia cycle length TCL plus the product of the number of pulses delivered n and the prematurity $P_i$ associated the pulses (RCL>=(TCL+n*P)) for Scenario F2. This scenario (Block 330) of incomplete peelback indicates that the the total prematurity $P_{TOTAL}$ of the ATP regimen was insufficient. Therefore, according to an embodiment of the present invention, device 10 increases the total prematurity $P_{total}$ of the next ATP regimen, Block 332, by increasing the prematurity $P_i$ of one or more pulses, or increasing the number of pulses n or some combination of the two. In one embodiment, the number of ATP pulses is increased by 50% and the prematurity $P_i$ associated with each ATP pulse is kept the same. The new pacing regimen is then delivered in Block 308, and the process continues as described above.

In scenario F2, the actual transit time $t_{transit}$ between electrode 15 and reentrant circuit 42 cannot be determined from the return cycle length RCL subsequent to the delivered ATP sequence because those ATP pulses never reached reentrant circuit 42. However, a minimum transit time $t_{transit}$ can be established based on the failure of the pacing regimen to reach reentrant circuit 42, where, for example, the minimum is at least one-half the total prematurity $P_{TOTAL}$ of the ATP sequence. This information is stored for future reference in determining the minimum number of pacing cycles initially required to reach reentrant circuit 42, both within the same tachycardia and applied to future tachycardias at Block 306 as previously discussed.

If device 10 determines that the return cycle length RCL is both not less than or equal to the tachycardia cycle length TCL, No in Block 321, and not greater than or equal to the sum of the tachycardia cycle length TCL and the total prematurity $P_{TOTAL}$, No Block 326, the device 10 determines that the return cycle length must therefore be greater than the tachycardia cycle length TCL but less than the sum of the tachycardia cycle length TCL and the total prematurity $P_{TOTAL}$, Block 334, and therefore concludes that the most recently delivered pacing regimen reached reentrant circuit 42 but failed to terminate the tachycardia, Block 335, i.e., the failure scenario is Scenario F3. Thus, the previous ATP regimen reached reentrant circuit 42 and entrained reentrant circuit 42, but it did not successfully terminate the tachycardia event occurring in reentrant circuit 42. Once device 10 determines it has reset reentrant circuit 42, Block 335, device 10 determines the transit time $t_{transit}$ from electrode 15 to the entrance to reentrant circuit 42 using the return cycle length Equations 2 and 3, Block 336. The transit time $t_{transit}$ solved for in Equation 3 is the actual travel time from electrode 15 to reentrant circuit 42, not an estimated time. Equation 2 describes the path of an ATP pulse that successfully reaches reentrant circuit 42 (traveling for transit time $t_{transit}$), enters and entrains reentrant circuit 42 (taking an amount of time equal to TCL), and then travels back to electrode 15 (traveling for time $t_{transit}$). This value is stored and identified with the particular characteristics of the tachycardia (e.g., TCL, electrical signal characteristics sensed by an electrode, or combination of both), Block 337. Device 10 may use stored $t_{transit}$ times to estimate future $t_{transit}$ times (e.g., at Block 303) associated with subsequent tachycardias. In addition, if the embodiment uses a maximum estimate of transit time $t_{transit}$ to select a number of pulses n in Block 306, the maximum estimate of transit time $t_{transit}$ is updated to the measured transit time $t_{transit}$ if the measure is longer.

After determining transit time $t_{transit}$, device 10 crafts a customized ATP sequence in Block 338. For example, device determines the minimum number of ATP pulses n required to complete peelback and reach reentrant circuit 42 in the same manner as in Block 306, but using the determined transit time $t_{transist}$. For the burst ATP example this can be done using Equation 4, in which $P_i=P$.

In general, once transit time $t_{transit}$ is measured via a return cycle length RCL from a reset scenario, device 10 can alter ATP pacing period $T_i$ and still calculate conclusively the number of ATP pulses n required to reach reentrant circuit 42 at the new pacing period. Typically, device 10 will generate at least one ATP pulse more than required to reach reentrant circuit 42. In addition, because return cycle length RCL indicates the prior therapy did interact with the tachycardia, it is determined that none of the prematurities $P_i$ to which reentrant circuit 42 was exposed were large enough to terminate excitability. Thus, the other step in customization is to produce a sequence where the pulses that reach reentrant circuit 42 produce a larger prematurity P than has been delivered in the past. In one embodiment, the prematurities $P_i$ of the previous ATP sequence are kept constant, the number of pulses n is selected to be one greater (n+1) than the number needed to reach reentrant circuit 42 based on the result of Equation 4, then an additional pace is provided at a more aggressive (higher) individual prematurity $P_i$. For the burst example under discussion, all prematurities $P_i$ are kept constant. Therefore, the delivery of a larger prematurity $P_i$ to the circuit raises all of the prematurities $P_i$. For burst customization, a larger prematurity P is selected, this is applied to the determined the tachycardia cycle length TCL to determine a new ATP pacing period $T_i$ for the burst sequence and via Equation 4 to determine the necessary number of pulses n to ensure interaction with reentrant circuit 42. After selecting the number of pulses n required and the cycle lengths $T_i$ (thus fully specifying the ATP regimen), Block 338, the customized ATP regimen is delivered, Block 308, and the process continues as described previously.

The example operation of FIG. 8 is only one of a variety of responses that RCL analysis makes possible. Application of the fundamental information discovered via the application of return cycle length RCL analysis of the invention allows more complex analysis incorporating a history of return cycle length RCL or transit time $t_{transit}$. As an illustrative example, the analysis to determine failure to capture is expanded to incorporate additional cases beyond return cycle length RCL and tachycardia cycle length TCL.

In this embodiment, at Block 320, an additional analysis identifies alternate manifestations of Scenario F1 (failure to capture). For instance, if the last ATP pulse ($ATP_N$) in the ATP regimen fails to capture, this could be indicative that the tissue surrounding electrode had not yet recovered (repolarized) from the previous ATP pulse ($ATP_{N-1}$) delivered. The result is that ATP pulse $ATP_N$ does not propagate towards reentrant circuit 42. This is typical in ATP pulsing regimens in which the last pulse is provided at a more aggressive pace (i.e., has a larger prematurity P than previous pulses). To determine if the last pulse failed to capture, PCD device 10 compares the return cycle length RCL associated with the current ATP regimen with an expected return cycle length RCL ($RCL_{expected}$). If a previous unsuccessful series resulted in the determination of transit time $t_{transit}$ for the tachycardia, then the expected return cycle length $RCL_{expected}$ for a series is approximately $2*t_{transit}+TCL$. Otherwise, device 10 can estimate the expected return cycle length $RCL_{expected}$ to some extent based on the relationship between total prematurity $P_{TOTAL}$ of the current ATP regimen and return cycle length RCL (i.e., as total prematurity $P_{TOTAL}$ increases, return cycle length also increases in linear fashion). This relationship gives an expected return cycle length $RCL_{expected}$ equal to $TCL+P_{TOTAL}$. Thus, device 10 can approximate, based on the total prematurity associated with the current ATP regimen and the expected return cycle length RCL.

Once the expected return cycle length $RCL_{expected}$ has been calculated by one of the method discussed above, it is compared with the current return cycle length $RCL_{current}$. If the current return cycle length $RCL_{current}$ is equal to the difference between the expected return cycle length $RCL_{expected}$ and the pacing period ($T_N$) of the last ATP pulse ($ATP_N$) in the ATP regimen (i.e. $RCL_{current}=RCL_{expected}-T_N$), then device 10 determines that the last ATP pulse ($ATP_N$) most likely failed to capture, but previous pulses were able to capture. In this case, device 10 lowers the prematurity $P_N$ of the last ATP pulse ($ATP_N$) in the ATP regimen and then delivers the pacing regimen (with less aggressively paced $ATP_N$), Block 308. In another embodiment, not only is prematurity $P_N$ of the last ATP pulse decreased, but an additional stimulus is added at the original prematurity $P_N$ of the prior sequence. In another embodiment, the prematurity $P_{N-1}$ of the penultimate pulse of the new ATP regimen is set to be less than the prematurity of the pulse that failed to capture. The prematurity $P_N$ of the final pulse is set to be greater than the prematurity $P_{N-1}$ of the penultimate pulse. In these embodiments, the reduced prematurity of the penultimate pulse conditions the local tissue such that the final pulse is more likely to capture.

According to the present invention, device 10 selects, based on detection of a tachycardia event, an initial number of pulses based on an estimated distance (i.e., transit time) between an electrode and a reentrant circuit located somewhere in the heart. After applying an initial ATP regimen, device 10 measures return cycle length RCL to determine the effect of the initial pacing regimen on the reentrant tachycardia. Device 10 uses return cycle length RCL to determine the effect of the previous pacing regimen on the tachycardia, i.e. failure to capture generally, failure to capture last pulse, failure to complete peelback, or resetting of reentrant circuit. Based on the return cycle length RCL, device 10 alters subsequent ATP regimens to more effectively terminate the reentrant tachycardia. Termination of the reentrant tachycardia is confirmed by a return to normal sinus rhythm.

While a particular embodiment of the present invention has been shown and described, modifications may be made. It is therefore intended in the appended claims to cover all such changes and modifications, which fall within the true spirit and scope of the invention.

We claim:

1. A medical device for delivering a plurality of pacing pulses to a patient having a heart generating cardiac signals to terminate a tachycardia event of a heart, the tachycardia event having a tachycardia cycle length, comprising:
   an electrode;
   a therapy module, electrically coupled to the electrode, delivering a first plurality of pacing pulses of the plurality of pacing pulses having a pacing pulse cycle length to the heart with the electrode in response to the tachycardia event;
   sensing circuitry, electrically coupled to the electrode, to detect the tachycardia event in response to cardiac signals sensed by the electrode; and
   a processor, electrically coupled to the therapy module and the sensing circuitry, wherein the processor controls the therapy module to deliver a second plurality of pacing pulses of the plurality of pacing pulses in response to the tachycardia event, at least one characteristic of the second plurality of pacing pulses being adjusted based, at least in part, on at least one of:
      a transit time associated with delivery of the plurality of pacing pulses, the transit time being a function of the tachycardia cycle length and a return cycle length representative of an amount of time between a last one of the first plurality of pacing pulses and the first one of the cardiac signals generated by the heart immediately following the first plurality of pacing pulses; and
      a prematurity defined by a difference in time between the tachycardia cycle length and a pacing cycle length defined by a time between individual ones of the plurality of pacing pulses.

2. The device of claim 1, wherein the transit time is one half of a difference between the return cycle length and the tachycardia cycle length.

3. The device of claim 1, wherein each individual one of a plurality of prematurities are defined by a difference in time between the tachycardia cycle length and the pacing cycle length, wherein a total prematurity associated with the first plurality of pacing pulses is equal to a sum of said plurality of prematurities, and wherein the processor controls the therapy module to deliver the second plurality of pacing pulses based, at least in part, on the total prematurity associated with the first plurality of pacing pulses.

4. The device of claim 3, wherein the total prematurity is greater than the transit time.

5. The device of claim 1, wherein the processor selects a number of pacing pulses of the second plurality of pacing pulses based, at least in part, on a distance between said electrode and a reentrant circuit.

6. The device of claim 5, wherein the number of pacing pulses of the second plurality of pacing pulses is a minimum number of pacing pulses based on the transit time corresponding to a distance between the electrode and a reentrant circuit and the prematurity.

7. A method of delivering a plurality of pacing pulses to a patient having a heart generating cardiac signals to terminate a tachycardia event of the heart, the tachycardia event having a tachycardia cycle length, comprising:
   sensing the cardiac signals generated by the heart;
   detecting the tachycardia event based, at least in part, on a cycle length of the cardiac signals; and delivering a first plurality of pacing pulses of the plurality of pacing pulses having a pacing pulse cycle length to the heart with the electrode in response to the tachycardia event;

delivering a second plurality of pacing pulses of the plurality of pacing pulses in response to the tachycardia event, at least one characteristic of the second plurality of pacing pulses being adjusted based, at least in part, on at least one of:

a transit time associated with delivery of the plurality of pacing pulses, the transit time being a function of the tachycardia cycle length and a return cycle length representative of an amount of time between a last one of the first plurality of pacing pulses and a first one of the cardiac signals generated by the heart immediately following the first plurality of pacing pulses; and a prematurity defined by a difference in time between the tachycardia cycle length and a pacing cycle length defined by a time between individual ones of the plurality of pacing pulses.

8. The method of claim 7, wherein the transit time is one half of a difference between the return cycle length and the tachycardia cycle length.

9. The method of claim 7, wherein each individual one of a plurality of prematurities are defined by a difference in time between the tachycardia cycle length and the pacing cycle length, wherein a total prematurity associated with the first plurality of pacing pulses is equal to a sum of said plurality of prematurities, and wherein the second plurality of pacing pulses is delivered based, at least in part, on the total prematurity.

10. The method of claim 9, the total prematurity is greater than the transit time.

11. The method of claim 7, wherein the second plurality of pacing pulses has a number of pacing pulses based, at least in part, on a distance between an electrode associated with delivering said plurality of pacing pulses and a reentrant circuit.

12. The method of claim 11, wherein the number of pacing pulses of the second plurality of pacing pulses is a minimum number of pacing pulses based on the transit time and the prematurity.

* * * * *